US010617638B2

(12) United States Patent
Bonelli et al.

(10) Patent No.: US 10,617,638 B2
(45) Date of Patent: Apr. 14, 2020

(54) STABLE PRESSURIZED AEROSOL SOLUTION COMPOSITION OF GLYCOPYRRONIUM BROMIDE AND FORMOTEROL COMBINATION

(71) Applicant: CHIESI FARMACEUTICI S.P.A., Parma (IT)

(72) Inventors: Sauro Bonelli, Parma (IT); Diego Copelli, Parma (IT); Massimiliano Dagli Alberi, Parma (IT); Francesca Usberti, Parma (IT); Enrico Zambelli, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 0 days.

(21) Appl. No.: 15/196,318

(22) Filed: Jun. 29, 2016

(65) Prior Publication Data

US 2016/0303045 A1 Oct. 20, 2016

Related U.S. Application Data

(63) Continuation of application No. PCT/EP2014/079259, filed on Dec. 23, 2014.

(30) Foreign Application Priority Data

Dec. 30, 2013 (EP) .................................... 13199784

(51) Int. Cl.
*A61K 31/40* (2006.01)
*A61K 9/12* (2006.01)
*A61K 9/00* (2006.01)
*A61K 31/167* (2006.01)
*A61K 47/10* (2017.01)
*A61M 15/00* (2006.01)
*A61K 31/573* (2006.01)
*A61K 31/58* (2006.01)
*A61K 45/06* (2006.01)
*A61M 39/22* (2006.01)

(52) U.S. Cl.
CPC .............. *A61K 9/124* (2013.01); *A61K 9/008* (2013.01); *A61K 31/167* (2013.01); *A61K 31/40* (2013.01); *A61K 31/573* (2013.01); *A61K 31/58* (2013.01); *A61K 45/06* (2013.01); *A61M 15/009* (2013.01); *A61M 15/0021* (2014.02); *A61M 15/0071* (2014.02); *A61M 15/0086* (2013.01); *A61M 39/22* (2013.01); *A61M 2039/226* (2013.01); *A61M 2205/0238* (2013.01)

(58) Field of Classification Search
CPC ........ A61K 31/40; A61K 31/167; A61K 9/12; A61K 47/10; A61K 47/08; A61K 9/00
See application file for complete search history.

(56) References Cited

U.S. PATENT DOCUMENTS

| 6,716,414 B2* | 4/2004 | Lewis ................... A61K 9/008 128/200.14 |
| 2004/0126325 A1 | 7/2004 | Lewis et al. |
| 2005/0130947 A1* | 6/2005 | Biggadike ............ A61K 9/0043 514/172 |
| 2006/0171899 A1* | 8/2006 | Adjei ..................... A61K 9/008 424/46 |
| 2007/0086953 A1* | 4/2007 | Meakin .................. A61K 9/008 424/45 |
| 2011/0132355 A1* | 6/2011 | Gerhart ................ A61K 9/0078 128/200.23 |
| 2015/0182450 A1* | 7/2015 | Bonelli ................... A61K 31/40 128/200.23 |
| 2015/0306026 A1* | 10/2015 | Bonelli .................. A61K 9/008 424/45 |
| 2015/0328144 A1* | 11/2015 | Bonelli .................. A61K 9/008 424/45 |
| 2016/0303044 A1* | 10/2016 | Bonelli .................. A61K 9/008 |
| 2017/0079949 A1* | 3/2017 | Bonelli .................. A61K 9/008 |
| 2017/0095444 A1* | 4/2017 | Bonelli .................. A61K 9/008 |
| 2019/0046433 A1* | 2/2019 | Bonelli .................. A61K 9/008 |

FOREIGN PATENT DOCUMENTS

| CO | 13284465 | 3/2014 |
| EP | 1157689 | * 11/2001 |
| EP | 2 201 934 | 6/2010 |
| WO | WO 2005074900 | * 8/2005 |
| WO | 2011/076841 | 6/2011 |
| WO | 2011/076843 | 6/2011 |
| WO | WO 2012/158166 A1 | 11/2012 |

OTHER PUBLICATIONS

Korean Office Action dated Jul. 19, 2017 in Korean Patent Application No. 10-2016-7020695 (submitting English translation only).
Reinhard Vehring, et al, "Cosuspensions of Microcrystals and engineered Microparticles for Uniform and Efficient Delivery of Respiratory Therapeutics from Pressurized Metered Dose Inhalers", Langmuir, vol. 28 No. 42, Sep. 17, 2012, pp. 15015-15023.
Extended European Search Report in Application No. 13199784.3 dated Feb. 26, 2014.
International Search Report in PCT/EP2014/079259 dated Dec. 23, 2014.
Office Action dated Nov. 15, 2017 in Colombian Patent Application 16-171.781 (submitting English version only), 5 pages.

* cited by examiner

*Primary Examiner* — Mina Haghighatian
(74) *Attorney, Agent, or Firm* — Oblon, McClelland, Maier & Neustadt, L.L.P.

(57) ABSTRACT

Aerosol solution compositions intended for use with a pressurized metered dose inhaler, comprising glycopyrronium bromide and formoterol, or a salt thereof or a solvate of said salt, optionally in combination with one or more additional active ingredients, and stabilized by a selected amount of a mineral acid, exhibit improved stability when contained in a can internally coated by a resin comprising a fluorinated ethylene propylene (FEP) polymer.

16 Claims, No Drawings

STABLE PRESSURIZED AEROSOL SOLUTION COMPOSITION OF GLYCOPYRRONIUM BROMIDE AND FORMOTEROL COMBINATION

CROSS REFERENCES TO RELATED APPLICATIONS

This application is a continuation of International Patent Application No. PCT/EP2014/079259, filed Dec. 23, 2014, and claims priority to European Patent Application No. 13199784.3, filed on Dec. 30, 2013, both of which are incorporated herein by reference in their entireties.

BACKGROUND OF THE INVENTION

Field of the Invention

The present invention relates to stable aerosol solution compositions, comprising glycopyrronium bromide and formoterol, or a salt thereof or a solvate of said salt, optionally in combination with an inhalation corticosteroid (ICS), stabilized by a mineral acid, which are contained in an aerosol can. The present invention also relates to methods for treating and/or preventing certain diseases and conditions by administering such a composition contained in such an aerosol can.

Discussion of the Background

Glycopyrronium bromide (also known as glycopyrrolate) is a muscarinic M3 anticholinergic agent used to reduce salivation associated with administration of certain anaesthetics, and as adjunctive therapy for peptic ulcers. It has also been reported to be effective in the treatment of asthmatic symptoms (Hansel et al., Chest 2005; 128:1974-1979, which is incorporated herein by reference in its entirety).

WO 2005/107873, which is incorporated herein by reference in its entirety, relates to the use of glycopyrrolate for the treatment of childhood asthma.

WO 01/76575, which is incorporated herein by reference in its entirety, discloses a controlled release formulation for pulmonary delivery of glycopyrrolate. The formulation is intended for use in the treatment of respiratory diseases, in particular of chronic obstructive pulmonary disease (COPD). The patent application focuses, essentially, on dry powder formulations suitable for delivery by means of a dry powder inhaler (DPI).

WO 2005/074918, which is incorporated herein by reference in its entirety, discloses combinations of glycopyrrolate with glucocorticoid drugs and their use for treating diseases of the respiratory tract.

WO 2005/110402, which is incorporated herein by reference in its entirety, discloses combinations of glycopyrrolate with a beta-2 agonist of the class of indane or of benzothiazole-2-one derivatives for the treatment of inflammatory or of obstructive airway diseases.

WO 2006/105401, which is incorporated herein by reference in its entirety, discloses combinations of an anticholinergic, a corticosteroid and a long-acting beta-2 agonist for the prevention and treatment of respiratory, inflammatory or obstructive airway diseases; glycopyrrolate is among the optional anticholinergic agents.

According to WO 2007/057223 and WO 2007/057222, both of which are incorporated herein by reference in their entireties, combinations of glycopyrronium bromide with an anti-inflammatory steroid, particularly mometasone furoate, are reported to provide a therapeutic benefit in the treatment of inflammatory and obstructive airways diseases.

WO 2007/057221 and WO 2007/057219, both of which are incorporated herein by reference in their entireties, respectively refer to combinations of a glycopyrronium salt with an indanyl derivative beta-2 agonist (or analogue) or with an anti-inflammatory steroid, particularly mometasone furoate.

WO 00/07567, which is incorporated herein by reference in its entirety, discloses, in example 4, a suspension aerosol formulation wherein to a mixture of micronized actives, namely formoterol fumarate, glycopyrronium bromide and disodium cromoglycate, a propellant mixture of HFA and dinitrogen monoxide, together with 2% by weight of ethanol, are added.

The "Martindale. The complete drug reference", January 2002, monograph on glycopyrronium bromide (page 467), which is incorporated herein by reference in its entirety, shows that in investigations on compatibility of this substance with aqueous infusion solutions for injections and additives, the stability of glycopyrronium bromide is questionable above a pH 6, owing to ester hydrolysis.

US 2002/025299, which is incorporated herein by reference in its entirety, discloses pressurized aerosol solution formulations of different active ingredients among which is formoterol or its combinations with beclometasone dipropionate, further acidified by HCl and stored in given cans such as stainless steel or anodized aluminum, or even lined with an inert organic coating.

WO 2005/074900, which is incorporated herein by reference in its entirety, discloses an inhalable combination of an anticholinergic agent with a beta-2 mimetic agent for the treatment of inflammatory or obstructive respiratory diseases and, in the examples shows formulations of the R,R-enantiomer of glycopyrronium bromide in combination with formoterol, either as DPI formulation or pMDI suspension.

US 2006/0257324, which is incorporated herein by reference in its entirety, discloses the delivery of a combination of two or more dissolved drugs in a HFA propellant-cosolvent system, substantially having the same particle size distribution and thus allowing for their co-deposition in the same lung region tract. These formulations comprise a beta-2 agonist (formoterol or carmoterol being exemplified) and a corticosteroid (beclometasone dipropionate being exemplified), or an anticholinegic agent such as ipratropium, oxitropium, tiotropium or glycopyrronium bromide, these latter being only generically cited in the description.

Formoterol is a beta-2 adrenergic agonist drug capable of relaxing smooth muscle in the bronchi and opening the airways to reduce wheezing conditions. It is commonly used in the management of asthma and other respiratory conditions.

Recently, an effective combination therapy comprising formoterol fumarate and beclometasone dipropionate (BDP) has become available under the trade-name Foster®. Said product is designed to be delivered to the lungs through a variety of aerosol means also including pressurized metered dose inhalers (pMDI).

In this respect, it is known that aerosol solutions of formoterol fumarate are relatively unstable and have a short shelf-life when stored under suboptimal conditions. To obviate to this drawback, Foster® composition has been properly developed by incorporating a suitable amount of inorganic acid in order to stabilize the formoterol component at a selected apparent pH range, for instance as described in EP 1 157 689, which is incorporated herein by reference in its entirety.

In WO 2011/076843, which is incorporated herein by reference in its entirety, it is disclosed pMDI aerosol solution formulations comprising glycopyrronium bromide in combination with formoterol or salts thereof, optionally including an inhalation corticosteroid such as BDP, wherein a suitable amount of a mineral acid was added, in particular 1M HCl in the range of 0.1-0.3 µg/µl, so that both formoterol and glycopyrronium bromide components were properly stabilized. In addition, the above compositions enabled to maintain the amount of a degradation product, therein referred to as DP3, to low levels.

However, when using relatively high amounts of acid as a stabilizing adjuvant to both formoterol and glycopyrronium components, the amount of DP3 being detected upon storage for 3 months at 25° C. and 60% of relative humidity (RH), were indeed remarkable.

Therefore, as disclosed in WO 2011/076843, which is incorporated herein by reference in its entirety, a further step comprising removal of oxygen from the aerosol canister headspace, for instance by incorporating an oxygen purging step through vacuum crimping in the process of filling the aerosol canister, may be thus required so as to lower DP3 content.

During the formulation development of such combinations, the degradation product DP3 was then identified as being N-(3-bromo)-[2-hydroxy-5-[1-hydroxy-2-[1-(4-methoxyphenyl)propan-2-ylamino]ethyl]phenyl]formamide (see analytical details in the experimental section).

As the formation of this degradation product, when it is quantified significantly above the identification/qualification threshold (≥1.0% w/w with respect to the theoretical formoterol fumarate content of 6 µg/actuation [as defined in ICH Guideline Q3B(R2)], which is incorporated herein by reference in its entirety) may represent a potential issue for these pMDI combination formulations, means for lowering DP3 content below an acceptable threshold, other than those known, involving oxygen removal and requiring a dedicated purging step in the filling of the aerosol canister during manufacturing, could be particularly advantageous.

As such, it would be thus desirable to provide a clinically useful aerosol combination product that combines the therapeutic benefits of formoterol or salts thereof or a solvate of said salt and glycopyrronium bromide, optionally in conjunction with additional active ingredients such as inhalation corticosteroids, in particular beclometasone dipropionate, so that each individual pharmaceutically active component is properly delivered to the lungs in effective and consistent doses over an extended product lifetime, and ideally without the need for particular storage conditions of temperature or humidity, that could be otherwise required to maintain low levels of degradation products such as DP3.

SUMMARY OF THE INVENTION

Accordingly, it is one object of the present invention to provide novel stable aerosol solution compositions, comprising glycopyrronium bromide and formoterol, or a salt thereof or a solvate of said salt, optionally in combination with an inhalation corticosteroid (ICS), stabilized by a mineral acid, which are contained in an aerosol can.

It is another object of the present invention to provide novel methods for treating and/or preventing certain diseases and conditions by administering such a composition contained in such an aerosol can.

These and other objects, which will become apparent during the following detailed description, have been achieved by the inventors' discovery that once suitably stored in aluminum cans which are internally coated by a resin comprising a fluorinated ethylene propylene (FEP) polymer, further equipped with standard valves, the amounts of degradation products formed during the shelf-life of such compositions, particularly of DP3 may be minimized even below the detection threshold as determined after storage under severe conditions of temperature and humidity.

Thus, the present invention provides aerosol solution compositions intended for use with a pressurized metered dose inhaler (pMDI), comprising glycopyrronium bromide and formoterol, or a salt thereof or a solvate of said salt, optionally in combination with an inhalation corticosteroid (ICS), stabilized by a selected amount of a mineral acid, said composition being contained in a metal can internally coated by a resin comprising a fluorinated ethylene propylene (FEP) polymer.

More in particular, the present invention provides for the above pMDI compositions that, when stored in the aforementioned coated cans for a prolonged period of time under severe conditions of temperature and relative humidity (RH), show an amount of degradation products, particularly of N-(3-bromo)-[2-hydroxy-5-[1-hydroxy-2-[1-(4-methoxyphenyl)propan-2-ylamino]ethyl]phenyl]formamide, well below the limit of quantification (i.e. lower than 0.10% w/w with respect to the theoretical formoterol fumarate content of 6 µg/actuation).

The present invention further relates to the use of such stable aerosol solution compositions in the prevention and therapy of airway diseases, particularly of obstructive respiratory disorders such as asthma and COPD.

More specifically, the present invention provides a pharmaceutical aerosol solution composition intended for use in a pressurized metered dose inhaler comprising:

(a) glycopyrronium bromide at a dosage in the range of from 5 to 26 µg per actuation;

(b) formoterol, or a salt thereof or a solvate of said salt, at a dosage in the range of from 1 to 25 µg per actuation;

(c) a HFA propellant;

(d) a co-solvent; and (e) a stabilizing amount of a mineral acid;

wherein said composition is contained in an aerosol can internally coated by a resin comprising a fluorinated ethylene propylene (FEP) polymer.

According to the present invention, the amount of the degradation product N-(3-bromo)-[2-hydroxy-5-[1-hydroxy-2-[1-(4-methoxyphenyl) propan-2-ylamino]ethyl]phenyl]formamide, hereinafter shortly referred to as DP3, is lower than 0.10% w/w with respect to the theoretical formoterol fumarate content of 6 µg/actuation, which is the limit of quantification, either when stored in accelerated conditions at 25° C. and 60% relative humidity (RH) for at least 6 months, or when stored for 1 month in accelerated conditions at 40° C. and 75% of relative humidity (RH).

Optionally, the composition further comprises an inhalation corticosteroid selected from the group consisting of beclometasone dipropionate, mometasone furoate, budesonide, flunisolide, fluticasone propionate, fluticasone furoate, ciclesonide, triamcinolone, triamcinolone acetonide, methylprednisolone, and prednisone.

In another aspect, the present invention provides an aerosol can internally coated by a resin comprising a fluorinated ethylene propylene (FEP) polymer for use with a pharmaceutical aerosol solution composition intended for use in a pressurized metered dose inhaler comprising:

(a) glycopyrronium bromide at a dosage in the range of from 5 to 26 µg per actuation;

(b) formoterol, or a salt thereof or a solvate of said salt at a dosage in the range of from 1 to 25 µg per actuation;
(c) a HFA propellant;
(d) a co-solvent;
(e) a stabilizing amount of a mineral acid; and
(f) optionally, an inhalation corticosteroid.

In yet another aspect, the present invention provides a method to lower the amount of degradation product N-(3-bromo)-[2-hydroxy-5-[1-hydroxy-2-[1-(4-methoxyphenyl) propan-2-ylamino]ethyl]phenyl]formamide (DP3) formed during the shelf-life of a pharmaceutical aerosol solution composition intended for use in a pressurized metered dose inhaler comprising:
(a) glycopyrronium bromide at a dosage in the range of from 5 to 26 µg per actuation;
(b) formoterol, or a salt or a solvate of said salt thereof at a dosage in the range of from 1 to 25 µg per actuation;
(c) a HFA propellant;
(d) a co-solvent;
(e) a stabilizing amount of a mineral acid; and
(f) optionally, an inhalation corticosteroid
said method comprising containing the above composition in an aerosol can internally coated by a resin comprising a fluorinated ethylene propylene (FEP) polymer.

In yet another aspect, the present invention provides the use of an aerosol can internally coated by a resin comprising a fluorinated ethylene propylene (FEP) polymer, as a container for a pharmaceutical aerosol solution composition intended for use in a pressurized metered dose inhaler comprising:
(a) glycopyrronium bromide at a dosage in the range of from 5 to 26 µg per actuation;
(b) formoterol, or a salt thereof or a solvate of said salt at a dosage in the range of from 1 to 25 µg per actuation;
(c) a HFA propellant;
(d) a co-solvent;
(e) a stabilizing amount of a mineral acid; and
(f) optionally, an inhalation corticosteroid.

In a further aspect, the present invention provides the use of an aerosol composition as above described for the prevention and/or treatment of an obstructive respiratory disorder, including asthma and COPD.

DETAILED DESCRIPTION OF THE PREFERRED EMBODIMENTS

It has been found unexpectedly that in a pharmaceutical aerosol solution composition intended for use in a pressurized metered dose inhaler comprising:
(a) glycopyrronium bromide at a dosage in the range from 5 to 26 µg per actuation;
(b) formoterol, or a salt thereof or a solvate of said salt at a dosage in the range from 1 to 25 µg per actuation;
(c) a HFA propellant;
(d) a co-solvent;
(e) a stabilizing amount of a mineral acid; and
(f) optionally, an inhalation corticosteroid.

by the use of a specific internally coated metal can comprising a fluorinated ethylene propylene (FEP) polymer it is possible to maintain the level of the degradation product N-(3-bromo)-[2-hydroxy-5-[1-hydroxy-2-[1-(4-methoxyphenyl) propan-2-ylamino]ethyl]phenyl]formamide, formed by interaction of formoterol and glycopyrronium bromide, when the composition is stored in accelerated conditions at 25° C. and 60% relative humidity (RH) for at least 6 months, lower than 0.10% w/w, which is the limit of quantification (with respect to the theoretical formoterol fumarate content of 6 µg/actuation), independently of the type of metering valve used.

The pressurized aerosol solution composition of the present combination manufactured with this specific canister, after storage for 6 months at 25° C. and 60% RH, in addition to maintaining the degradation product DP3 level lower than the limit of quantification of 0.10% w/w (with respect to the theoretical formoterol fumarate content of 6 µg/actuation) showed an overall formoterol degradation products level within acceptable limits lower than 10% w/w (with respect to the theoretical formoterol fumarate content of 6 µg/actuation), preferably lower than 3% w/w and most preferably lower than 2% w/w and maintained the residual level of formoterol fumarate, the most instable component of the composition, higher than 90% w/w, preferably higher than 92% and most preferably higher than 95% w/w, with respect to its initial content.

Glycopyrronium bromide and the optional inhalation corticosteroid levels were maintained almost the same as the respective initial levels.

Other kinds of cans, internally coated with different polymers or passivation technologies, available in the market were not able to keep under control the formation of said specific degradation product and the relevant chemical stability profile of the components of said combination.

Glycopyrronium bromide, chemically defined as 3-[(cyclopentylhydroxyphenylacetyl)oxy]-1,1-dimethylpyrrolidinium bromide, has two chiral centres corresponding to four potential different stereoisomers with configurations (3R,2'R), (3S,2'R), (3R,2'S), and (3S,2'S). Glycopyrronium bromide in the form of any of these pure enantiomers or diastereomers or any combination thereof may be used in practising the present invention. In one embodiment of the invention the (3S,2'R), (3R,2'S)-3-[(cyclopentylhydroxyphenylacetyl)oxy]-1,1-dimethylpyrrolidinium bromide racemic mixture, defined as the threo mixture, also known as glycopyrrolate, is preferred. Glycopyrronium bromide is present in the formulation in an amount of 0.005 to 0.14% (w/w), preferably 0.008 to 0.090% (w/w), more preferably 0.01 to 0.045% (w/w), wherein % (w/w) means the amount by weight of the component, expressed as percent with respect to the total weight of the composition.

Glycopyrrolate is commercially available, and can be synthesized according to the process described in U.S. Pat. No. 2,956,062 or in Franko BV and Lunsford CD, J Med Pharm Chem 2(5), 523-540, 1960, both of which are incorporated herein by reference in their entireties.

Formoterol, normally used in therapy as the racemic mixture (R,R), (S,S) is chemically defined as (±),(R*,R*)—N-[2-hydroxy-5-[1-hydroxy-2-[1-(4-methoxyphenyl)propan-2-ylamino]ethyl]phenyl]formamide, can be in the form of the free base, or as a salt or a solvate thereof. Preferably the formoterol is provided in the form of its fumarate salt and more preferably the solvate form of the formoterol salt is formoterol fumarate dihydrate. Formoterol fumarate can, for instance, be employed in the formulation in an amount of 0.002 to 0.08% w/w, preferably 0.005 to 0.02% w/w.

It is preferred that the pharmaceutically active components of the composition are completely and homogeneously dissolved in the mixture of propellant and co-solvent, i.e. the composition is preferably a solution formulation.

Being that the present invention relates to a solution formulation wherein the active ingredients are completely dissolved in the formulation, when the description generically cites formoterol fumarate, both the forms of formoterol fumarate and formoterol fumarate dihydrate, which is its solvate form available in the market, are intended.

The co-solvent incorporated into the formulations of the invention has a higher polarity than that of the propellant and may include one or more substances such as a pharmaceutically acceptable alcohol or polyol in an amount capable to solubilize the pharmaceutically active components of the composition (formoterol fumarate, glycopyrronium bromide and optionally an inhalation corticosteroid) in the propellant.

Advantageously the alcohol co-solvent is selected from the group of lower branched or linear alkyl ($C_1$-$C_4$) alcohols such as ethanol and isopropyl alcohol. Preferably the co-solvent is ethanol.

Advantageously the polyol cosolvent is selected from glycerol, propylene glycol or polyethylene glycol.

The concentration of the co-solvent will vary depending on the final concentration of the active ingredient in the formulation and on the type of propellant. For example ethanol may be used in a concentration of 5 to 30% (w/w), preferably 8 to 25% (w/w), more preferably 10 to 15% (w/w). In one of the preferred embodiments the concentration of ethanol is about 12% (w/w).

The propellant component of the composition may be any pressure-liquefied propellant and is preferably a hydrofluoroalkane (HFA) or a mixture of different HFAs, more preferably selected from the group consisting of HFA 134a (1,1,1,2-tetrafluoroethane), HFA 227 (1,1,1,2,3,3,3-heptafluoropropane), and mixtures thereof. The preferred HFA is HFA 134a. HFAs may be present in the composition in an amount in the range of 70 to 95% (w/w), preferably 85 to 90% (w/w).

The ratio of propellant to co-solvent in the composition is 70:30 to 95:5 (w/w).

The stabilizing amount of a mineral acid, sufficient to stabilize glycopyrronium bromide and formoterol, is an amount of acid equivalent to 1M hydrochloric acid (HCl) in the range of 0.1 to 0.3 µg/µl of formulation, preferably 0.15 to 0.28 µg/µl, more preferably 0.18 to 0.26 µg/µl, even more preferably 0.200 to 0.240 µg/µl, most preferably 0.200 to 0.227 µg/µl and in particular 0.213 to 0.222 µg/µl of formulation.

HCl of different molarity or alternative inorganic acids (mineral acids) may be substituted for 1M HCl in the composition of the invention. For instance, using an acid at a concentration different from 1M HCl, its amount must be proportioned with respect to the concentration, according to calculation steps known to the skilled person.

Alternative acids may be any pharmaceutically acceptable monoprotic or polyprotic acid, such as (but not limited to): hydrogen halides (hydrochloric acid, hydrobromic acid, hydroiodic acid etc.) phosphoric acid, nitric acid, sulphuric acid, and halogen oxoacids.

Optionally, the aerosol solution composition may comprise other pharmaceutical excipients or additives known in the art. In particular, the compositions of the invention may comprise one or more low volatility components. Low volatility components are useful in order to increase the mass median aerodynamic diameter (MMAD) of the aerosol particles upon actuation of the inhaler and/or to improve the solubility of the active ingredient in the propellant/co-solvent mixture.

The low volatility component, when present, has a vapour pressure at 25° C. lower than 0.1 kPa, preferably lower than 0.05 kPa. Examples of low-volatility components are esters such as isopropyl myristate, ascorbyl myristate, tocopherol esters; glycols such as propylene glycol, polyethylene glycol, glycerol; and surface active agents such as saturated organic carboxylic acids (e.g. lauric, myristic, stearic acid) or unsaturated carboxylic acids (e.g. oleic or ascorbic acid).

The amount of low volatility component may vary from 0.1 to 10% w/w, preferably from 0.5 to 5% (w/w), more preferably between 1 and 2% (w/w).

In another embodiment an amount of water comprised between 0.005 and 0.3% (w/w) may optionally be added to the compositions in order to favourably affect the solubility of the active ingredient without increasing the MMAD of the aerosol droplets upon actuation.

Advantageously, the compositions of the invention are free of excipients (such as surfactants) other than co-solvent, propellant and a stabilizing amount of an acid.

The pharmaceutical compositions of the present invention may further comprise one or more additional pharmaceutically active agent for separate, sequential or simultaneous use. The one or more additional pharmaceutically active agent of the composition includes any active ingredient known in the art for prophylaxis or treatment of respiratory diseases and their symptoms. Examples of one or more additional pharmaceutically active agent are selected from the following classes:

beta-2 agonist, selected from the group of salbutamol, fenoterol, carmoterol (TA-2005; CHF 4226), indacaterol, milveterol, vilanterol (GSK 642444), olodaterol, abediterol, terbultaline, salmeterol, bitolterol, metaproterenol and a salt thereof, optionally in form of a single stereoisomer or of a mixture thereof;

inhalation corticosteroid, selected from the group of beclometasone dipropionate, budesonide or its 22R-epimer, ciclesonide, flunisolide, fluticasone propionate, fluticasone furoate, mometasone furoate, butixocort, triamcinolone acetonide, triamcinolone, methylprednisolone, prednisone, loteprednol and rofleponide;

anti-muscarinic drug selected from methscopolamine, ipratropium, oxitropium, trospium, tiotropium, aclidinium and umeclidinium as bromide salt or a salt with any other pharmaceutically acceptable counter ion; and phosphodiesterase-4 (PDE-4) inhibitor selected from CHF 6001, cilomilast, roflumilast, tetomilast, oglemilast and a salt thereof.

In a preferred embodiment, the composition of the present invention comprises an inhalation corticosteroid selected from beclometasone dipropionate (BDP), budesonide, fluticasone furoate, fluticasone propionate and mometasone furoate in addition to formoterol fumarate and glycopyrronium bromide components. In that embodiment the more preferred inhalation corticosteroid is selected from BDP and budesonide. BDP or budesonide are present in an amount of 0.02 to 0.8% w/w, more preferably 0.042 to 0.43% w/w. The most preferred inhalation corticosteroid is BDP.

The compositions of the present invention can be inhaled from any suitable known pressurized MDI device. Desired doses of the individual pharmaceutically active components of the formulation are dependent on the identity of the component and the type and severity of the disease condition, but are preferably such that a therapeutic amount of the active ingredient is delivered in one or two actuations. Generally speaking, doses of active ingredient are 0.5 to 1000 μg per actuation, e.g. about 1 to 300 μg/actuation, and sometimes about 5 to 150 μg/actuation. The skilled person in the field is familiar with how to determine the appropriate dosage for each individual pharmaceutically active ingredient.

With reference to formoterol fumarate in its dihydrate form, the preferred dosage is 1 to 24 μg per actuation, more preferably 6 to 12 µg per actuation. In a specific embodiment, the dose of formoterol fumarate dihydrate is of 6 or 12 µg per actuation.

With reference to glycopyrronium bromide, the preferred dosage is 5 to 26 µg per actuation more preferably 6 to 25 µg per actuation. In a specific embodiment, the dose of glycopyrronium bromide is 6, 12.5, or 25 µg per actuation.

With reference to the optional component, when it is selected from an inhalation corticosteroid, the preferred dosage is 20 to 1000 µg per actuation, preferably 50 to 250 µg per actuation. In specific embodiments, the dose of beclometasone dipropionate and of budesonide is 50, 100, or 200 µg per actuation.

The pharmaceutical composition of the present invention is filled into pMDI devices known in the art. Said devices comprise a can fitted with a metering valve. Actuation of the metering valve allows a small portion of the spray product to be released.

Part or all of the cans known in the art may be made of a metal, for example aluminum, aluminum alloy, stainless steel, or anodized aluminum. Alternatively the canister may be a plastic can or a plastic-coated glass bottle.

Metal canisters for pMDI may have part or all of their internal surfaces lined or passivated with an inert organic or inorganic coating applied by conventional coating or by plasma coating. Examples of coatings are epoxy-phenol resins, perfluorinated polymers such as perfluoroalkoxyalkane, perfluoroalkoxyalkylene, perfluoroalkylenes such as poly-tetratluoroethylene (Teflon), fluorinated-ethylene-propylene (FEP), polyether sulfone (PES) or fluorinated-ethylene-propylene polyether sulfone (FEP-PES) mixtures or combination thereof. Other suitable coatings could be polyamide, polyimide, polyamideimide, polyphenylene sulfide or their combinations.

According to the present invention, the cans have their internal surface coated with a resin comprising a FEP polymer or a FEP-PES mixture.

Suitable cans are available from manufacturers such as, for instance, 3M, Presspart and Pressteck.

The can is closed with a metering valve for delivering a therapeutically effective dose of the active ingredients. Generally the metering valve assembly comprises a ferrule having an aperture formed therein, a body moulding attached to the ferrule which houses the metering chamber, a stem consisting of a core and a core extension, an inner- and an outer-seal around the metering chamber, a spring around the core, and a gasket to prevent leakage of propellant through the valve.

The gasket seal and the seals around the metering valve may comprise elastomeric material selected from EPDM (ethylene propylene diene monomer), neoprene and butyl rubber. Among the butyl rubber chlorobutyl and bromobutyl rubber are preferably selected. EPDM rubber is particularly preferred.

The metering chamber, core and core extension are manufactured using suitable materials such as stainless steel, polyesters (e.g. polybutyleneterephthalate (PBT)), or acetals. The spring is manufactured in stainless steel eventually including titanium. The ferrule may be made of a metal, for example aluminum, aluminum alloy, stainless steel or anodized aluminum. Suitable valves are available from manufacturers such as, for instance, Valois-Aptar, Bespak ple, V.A.R.I., 3M-Neotechnic Ltd, Rexam, Coster.

The pMDI is actuated by a metering valve capable of delivering a volume of 25 to 150 µl, preferably 50 to 100 µl, and more preferably 50 µl or 63 µl per actuation.

Each filled canister is conveniently fitted into a suitable channeling device prior to use to form a metered dose inhaler for administration of the medicament into the lungs of a patient. Suitable channeling devices comprise, for example a valve actuator and a cylindrical or cone-like passage through which medicament may be delivered from the filled canister via the metering valve to the mouth of a patient e.g. a mouthpiece actuator.

In a typical arrangement, the valve stem is seated in a valve stem receptacle into the nozzle block which has an orifice leading to an expansion chamber. The expansion chamber has an exit orifice which extends into the mouthpiece. Actuator exit orifices having a diameter of 0.15 to 0.45 mm and a length from 0.30 to 1.7 mm are generally suitable. Preferably, an orifice having a diameter of 0.2 to 0.45 mm is used, e.g. 0.22, 0.25, 0.30, 0.33, or 0.42 mm.

In certain embodiments of the present invention, it may be useful to utilize actuator orifices having a diameter of 0.10 to 0.22 mm, in particular 0.12 to 0.18 mm, such as those described in WO 03/053501, which is incorporated herein by reference in its entirety. The use of said line orifices may also increase the duration of the cloud generation and hence, may facilitate the coordination of the cloud generation with the slow inspiration of the patient.

Suitable actuators for the delivery of the composition of the present invention are the conventional ones, wherein the longitudinal axis of the can (aligned with the longitudinal axis of the valve stem receptacle) is inclined of an angle greater or equal to 90° with respect to the longitudinal axis of the mouthpiece which is in general aligned with actuator orifice, but also an actuator according to WO 2012/032008, which is incorporated herein by reference in its entirety, wherein the longitudinal axis of the actuator exit orifice is aligned with the longitudinal axis of the valve stem receptacle, may be used.

Other suitable actuators for the delivery of the composition of the present invention are those disclosed in WO 2014/033057, which is incorporated herein by reference in its entirety, wherein the nozzle block orifice is characterised by the presence of a tubular element extending in the mouthpiece portion from the orifice aperture in a longitudinal axis aligned with a longitudinal axis of the mouthpiece portion. In particular said tubular element is positioned to enclose the orifice aperture within a recess.

In case the ingress of water into the formulation is to be avoided, it may be desired to overwrap the MDI product in a flexible package capable of resisting water ingress. It may also be desirable to incorporate a material within the packaging which is able to adsorb any propellant and co-solvent which may leak from the canister (e.g. silica gel or a molecular sieve).

Optionally, the MDI device filled with the composition of the present invention may be utilized together with suitable auxiliary devices favoring the correct use of the inhaler. Said auxiliary devices are commercially available and, depending on their shape and size, are known as "spacers", "reservoirs" or "expansion chambers". Volumatic™ is, for instance, one of the most widely known and used reservoirs, while Aerochamber™ is one of the most widely used and known spacers. A suitable expansion chamber is reported for example in WO 01/49350, which is incorporated herein by reference in its entirety.

The composition of the present invention may also be used with common pressurized breath-activated inhalers, such as those known with the registered names of Easi-Breathe™ and Autohaler™.

In addition the composition of the present invention may be administered through an actuator provided with a mechanical or electronic dose counter or dose indicator known in the art which may be top-mounted externally to the actuator or integrated internally to the actuator. Such a dose counter or dose indicator may show, respectively, the number or the range of the doses administered and/or the number or the range of the doses still remaining into the can.

The efficacy of an MDI device is a function of the dose deposited at the appropriate site in the lungs. Deposition is affected by the aerodynamic particle size distribution of the formulation which may be characterised in vitro through several parameters.

The aerodynamic particle size distribution of the composition of the present invention may be characterized using a cascade impactor according to the procedure described in the European Pharmacopoeia $7^{th}$ edition, 2013 (7.8), part 2.9.18, which is incorporated herein by reference in its entirety. An Apparatus E, operating at a flow rate range of 30 l/min to 100 l/min is used. Deposition of the drug on each cascade impactor cup is determined by high performance liquid chromatography (HPLC).

The following parameters of the particles emitted by a pressurized MDI may be determined:
i) mass median aerodynamic diameter (MMAD) is the diameter around which the mass aerodynamic diameters of the emitted particles are distributed equally;
ii) delivered dose is calculated from the cumulative deposition in the cascade impactor, divided by the number of actuations per experiment;
iii) respirable dose (fine particle dose=FPD) corresponds to the mass of particles of diameter≤5 microns, divided by the number of actuations per experiment;
iv) respirable fraction (fine particle fraction=FPF) is the percent ratio between the respirable dose and the delivered dose; and
v) "superfine" dose is obtained from the deposition from cup 6 (C6) to filter, corresponding to particles of diameter≤1.4 microns, divided by the number of actuations per experiment.

The solutions of the present invention are capable of providing, upon actuation of the pMDI device in which they are contained, a total FPF higher than 25%, preferably higher than 30%, more preferably higher than 35%.

Moreover, the compositions of the present invention are capable of providing, upon actuation, a fraction higher than or equal to 15% of emitted particles of diameter equal to or less than 1.4 microns as defined by the content cups from C6 to filter (C6-F) of the cascade impactor, relative to the total fine particle dose collected in the cups from C3 to filter (C3-F) of the impactor. Preferably the fraction of emitted particles of diameter equal to or less than 1.4 microns is higher than or equal to 20%, more preferably higher than 25%.

According to a further aspect of the present invention there is provided a method of filling an aerosol inhaler with a composition of the invention. Conventional bulk manufacturing methods and machinery well known in the art of pharmaceutical aerosol manufacture may be employed for the preparation of large-scale batches for the commercial production of filled canisters.

A first method comprises:
a) preparing a solution of glycopyrronium bromide, formoterol fumarate and optionally of the inhalation corticosteroid, preferably selected from beclometasone dipropionate and budesonide, in a co-solvent (e.g. ethanol), mineral acid, propellant comprising a HFA and an optional low volatility component at a temperature from −50 to −60° C. at which the composition does not vaporize;
b) cold-filling the can with the prepared solution; and
c) placing the valve onto the empty can and crimping.

An alternative method comprises:
a) preparing a solution of glycopyrronium bromide, formoterol fumarate and optionally of the inhalation corticosteroid, preferably selected from beclometasone dipropionate and budesonide, in a co-solvent (e.g. ethanol), mineral acid, and an optional low volatility component;
b) filling the open can with the bulk solution;
c) placing the valve onto the can and crimping; and
d) pressure-filling the can with the HFA propellant through the valve A further alternative method comprises:
a) preparing a solution of glycopyrronium bromide, formoterol fumarate and optionally of the inhalation corticosteroid, preferably selected from beclometasone dipropionate and budesonide, in a co-solvent (e.g. ethanol), mineral acid, a propellant comprising a HFA and an optional low volatility component using a pressurized vessel;
b) placing the valve onto the empty can and crimping; and
c) pressure-filling the can with the final solution through the valve In one embodiment of the present invention, oxygen is substantially removed from the headspace of the aerosol canister using conventional techniques in order to further stabilize the formoterol component, especially at higher acid concentrations. This can be achieved in different ways depending on the method of filling the container. Purging can be achieved by vacuum crimping or by using propellant, for instance. In a preferred embodiment the second filling method described above is modified to incorporate an oxygen purging step into step (c) by vacuum crimping.

The packaged composition of the present invention is stable for extended periods of time when stored under normal conditions of temperature and humidity. In a preferred embodiment the packaged composition are stable for over 6 months at 25° C. and 60% RH, more preferably for at least 9 months. Stability is assessed by measuring content of residual active ingredient and content of impurities/degradation products. A "stable" composition as defined herein means that the content of residual active ingredient is of at least about 90% w/w (which is the content percent by weight with respect to its initial content at time 0), preferably of at least about 95% w/w, and that the total content of degradation product is of not more than about 10% by weight with respect to initial content of the active ingredient at time 0, preferably of not more than about 5% by weight, at a given time point, as measured by HPLC/UV-VIS.

The optimized stable compositions meet the specifications required by the ICH Guideline Q1A(R2), which is incorporated herein by reference in its entirety, relevant for drug product stability testing for the purposes of drug registration.

The combination product compositions of the present invention may be used for prophylactic purposes or therapeutic purposes or for symptomatic relief of a wide range of conditions, and in one aspect the invention therefore relates to use of any of these pharmaceutical compositions as a medicament. In particular, the combination products of the present invention are useful in the prevention or treatment of many respiratory disorders, such as asthma of all types and chronic obstructive pulmonary disease (COPD).

Thus, in another aspect, the present invention relates to a method of preventing and/or treating a respiratory disease, such as asthma and COPD, comprising administering to a patient in need of such treatment a therapeutically effective amount of a pharmaceutical composition according to the invention.

The present invention also provides the use of the pharmaceutical compositions of the invention for the therapeutic or palliative treatment or prevention of respiratory diseases and their symptoms.

Respiratory disorders for which use of the pharmaceutical compositions of the present invention may also be beneficial are those characterized by obstruction of the peripheral airways as a result of inflammation and presence of mucus, such as chronic obstructive bronchiolitis, chronic bronchitis, emphysema, acute lung injury (ALI), cystic fibrosis, rhinitis, and adult or acute respiratory distress syndrome (ARDS).

Other features of the invention will become apparent in the course of the following descriptions of exemplary embodiments which are given for illustration of the invention and are not intended to be limiting thereof.

EXAMPLES

Example 1

Stability of a Triple Combination Aerosol Solution Composition Stored for 6 Months at 25° C. and 60% Relative Humidity (RH).

A study was performed to investigate the stability of a triple combination of formoterol fumarate (FF), glycopyrronium bromide (GLY), and beclometasone dipropionate (BDP) in an aerosol solution formulation whose composition is shown in Table 1 and which was stored for 6 months at 25° C. and 60% relative humidity (RH), in different kinds of can, crimped with different kinds of valve.

TABLE 1

Composition of the aerosol solution composition of the triple combination of formoterol fumarate (FF) dihydrate, glycopyrronium bromide (GLY), and beclometasone dipropionate (BDP). Content % w/w means the percent content by weight of each component with respect to the total weight of the composition.

| Component | Mass in µg per actuation (63 µL) | Mass in µg/µL | Content % (w/w) |
|---|---|---|---|
| BDP | 100 | 1.59 | 0.135 |
| FF dihydrate | 6 | 0.095 | 0.0081 |
| GLY | 12.5 | 0.20 | 0.0169 |
| Ethanol (anhydrous) | 8856 | 140.57 | 12.000 |
| 1M HCl | 14 | 0.22 | 0.0019 |
| HFA 134a | 64811.5 | 1028.75 | 87.820 |

Sample batches were stored in inverted orientation, deemed the worst case condition for the drug product stability, and 3 canisters for each batch were analyzed for residual content of active ingredients and total formoterol degradation products (including DP3: corresponding to N-(3-bromo)-[2-hydroxy-5-[1-hydroxy-2-[1-(4-methoxyphenyl) propan-2-ylamino]ethyl]phenyl]formamide) at the 6 months checkpoint.

The DP3 structure was identified by HPLC/MS/MS experiments performed on degraded samples of a triple combination of formoterol fumarate, glycopyrronium bromide, and beclometasone dipropionate in an aerosol solution formulation To attribute the position of the substituting bromine atom, a triple combination of deuterated formoterol fumarate (N-(3-deutero)-[2-hydroxy-5-[1-hydroxy-2-[1-(4-methoxyphenyl)propan-2-ylamino]ethyl]phenyl]formamide), glycopyrronium bromide, and beclometasone dipropionate was manufactured in plain aluminum cans, crimped with valves provided with EPDM (ethylene propylene diene monomer) rubber seals (RB700 from Bespak) and stored at 40° C. and 75% RH for 1 month. The analysis of the degradation products pointed out that the deuterium atom of deuterated formoterol fumarate was substituted by the bromine atom giving the degradation product DP3. Moreover N-(3-bromo)-[2-hydroxy-5-[1-hydroxy-2-[1-(4-methoxyphenyl) propan-2-ylamino]ethyl]phenyl]formamide standard was synthesized and characterized by $^1$H-NMR and MS/MS analysis. MS/MS spectrum of N-(3-bromo)-[2-hydroxy-5-[1-hydroxy-2-[1-(4-methoxyphenyl) propan-2-ylamino]ethyl]phenyl]formamide standard showed a fragmentation pattern comparable to the fragmentation pattern of DP3.

The residual content of each active ingredient, DP3 and the total amount of formoterol degradation products were measured using a validated HPLC/UV-VIS method. A mass spectra detector was used to confirm the molecular weights of the detected degradation products found in each can.

The results, summarized in the following Table 2 showed that, after 6 months at 25° C./60% relative humidity (RH), the configurations performing the best results in terms of higher active ingredient content (in particular of glycopyrronium bromide and formoterol), the lowest levels of total formoterol degradation products (with respect to the theoretical formoterol fumarate content of 6 µg/actuation) and, unexpectedly, in degradation product DP3 lower than the limit of quantification of 0.10% w/w (with respect to theoretical formoterol fumarate content of 6 µg/actuation), were those wherein the composition was stored in aluminum cans internally coated with a resin comprising a fluorinated ethylene propylene (FEP) polymer.

Even if as known from WO 2011/076843, which is incorporated herein by reference in its entirety, cited above, vacuum crimping improves the stability of the composition by oxygen removal from the aerosol can; unexpected improvements to the stability were indeed obtained by using FEP coated cans.

The composition of the present invention packaged in cans internally coated with a resin comprising a fluorinated ethylene propylene (FEP) polymer showed degradation product DP3 level lower than the limit of quantification of 0.10% w/w (with respect to the theoretical formoterol fumarate content of 6 µg/actuation), total formoterol degradation product levels lower than 2% w/w (with respect to the theoretical formoterol fumarate content of 6 µg/actuation) and the maintenance of formoterol fumarate, the most instable component of the composition, residual level higher than 95% w/w after storage in the present conditions.

TABLE 2

Results of the stability test of Example 1 performed on the composition stored for 6 months at 25° C. and 60% relative humidity (RH).

| Can | Valve | Crimping | Residual FF (% w/w) | Residual GLY (% w/w) | Residual BDP (% w/w) | DP3 (% w/w with respect to the theoretical formoterol fumarate content) | Total Amount of Formoterol degradation products (% w/w with respect to the theoretical formoterol fumarate content) |
|---|---|---|---|---|---|---|---|
| FEP coated aluminum | EPDM 1 | Normal | 97.0 | 99.2 | 99.5 | <0.10 | 1.6 |
| FEP coated aluminum | EPDM 1 | Vacuum | 96.9 | 98.9 | 99.3 | <0.10 | 1.6 |
| FEP coated aluminum | EPDM 2 | Normal | 98.6 | 100.2 | 99.0 | <0.10 | 1.8 |
| FEP coated aluminum | EPDM 2 | Vacuum | 99.6 | 100.8 | 99.6 | <0.10 | 1.6 |
| FEP coated aluminum | EPDM 3 | Normal | 96.1 | 98.5 | 97.9 | <0.10 | 0.58 |
| FEP coated aluminum | EPDM 4 | Normal | 97.7 | 99.0 | 99.4 | <0.10 | 1.5 |
| FEP coated aluminum | EPDM 4 | Vacuum | 96.3 | 98.6 | 99.1 | <0.10 | 0.74 |
| FEP coated aluminum | EPDM 5 | Normal | 99.1 | 100.3 | 99.2 | <0.10 | 1.3 |
| FEP coated aluminum | EPDM 5 | Vacuum | 98.2 | 100.0 | 98.9 | <0.10 | 1.8 |
| Plasma coated aluminum 2 | EPDM 2 | Normal | 74.5 | 99.1 | 99.7 | 8.98 | 16.0 |
| Plasma coated aluminum 2 | EPDM 2 | Vacuum | 91.8 | 101.2 | 100.6 | 3.40 | 5.6 |
| Plasma coated aluminum 2 | EPDM 4 | Normal | 94.8 | 98.4 | 98.3 | 1.21 | 2.6 |
| Plasma coated aluminum 2 | EPDM 4 | Vacuum | 85.2 | 98.5 | 98.6 | 5.00 | 8.1 |
| Plasma coated aluminum 2 | EPDM 5 | Normal | 93.5 | 99.2 | 99.7 | 1.9 | 3.7 |
| Anodized aluminum | EPDM 2 | Normal | 84.6 | 96.5 | 99.4 | 1.4 | 4.9 |
| Anodized aluminum | EPDM 3 | Normal | 89.0 | 98.0 | 99.1 | 0.41 | 4.6 |
| Plasma coated aluminum 3 | EPDM 2 | Normal | 90.6 | 98.7 | 99.8 | 1.8 | 3.1 |
| Fluorine passivated aluminum surface | EPDM 2 | Normal | 70.0 | 96.8 | 99.7 | 10.4 | 14.0 |
| Fluorine passivated aluminum surface | EPDM 3 | Normal | 82.4 | 97.8 | 99.7 | 5.2 | 8.0 |
| Anodized aluminum | EPDM 6 | Normal | 73.8 | 85.8 | 96.5 | 1.43 | 11.9 |
| Anodized aluminum | EPDM 3 | Normal | 83.0 | 94.4 | 97.3 | 0.74 | 5.4 |
| Fluorine passivated aluminum surface 2 | EPDM 6 | Normal | 86.0 | 95.8 | 94.5 | 1.97 | 5.6 |
| Plasma coated aluminum 3 | EPDM 6 | Normal | 88.0 | 96.0 | 94.2 | 0.66 | 2.5 |
| Fluorine passivated aluminum surface 2 | EPDM 3 | Normal | 82.0 | 96.8 | 97.3 | 5.78 | 10.4 |
| Plasma coated aluminum 3 | EPDM 3 | Normal | 76.8 | 96.0 | 97.5 | 0.17 | 4.3 |

% (w/w), unless specifically defined, relates to the content by weight of each substance with respect to its initial content in the formulation.
Different numbers near each valve or can definitions define different kinds of cans or valves from same or different suppliers as below reported: Valves: EPDM 1 to 3 represent respectively Bespak: RB700, BK700, and BK701; EPDM 4 to 6 represent respectively Aptar 808, 810, and 820; Cans: FEP coated from 3M; Anodized aluminum, Plasma coated aluminum 2 and 3 and fluorine passivated aluminum surface cans were from Presspart.

Example 2

Stability of a Triple Combination Aerosol Solution Composition Stored for 1 Month at 40° C. and 75% Relative Humidity (RH)

A further study was performed to investigate the stability of the triple combination of formoterol fumarate (FF), glycopyrronium bromide (GLY), and beclometasone dipropionate (BDP) in an aerosol solution formulation with the same composition as shown in Table 1 of Example 1 and which was stored in more stressed conditions, and in particular for 1 month at 40° C. and 75% relative humidity (RH), using different kinds of can, crimped with different kinds of valve.

Sample batches were stored in inverted orientation, deemed the worst case condition for the drug product stability and 3 canisters for each batch were analyzed for residual content of active ingredients and total formoterol degradation products (including DP3: corresponding to N-(3-bromo)-[2-hydroxy-5-[1-hydroxy-2-[1-(4-methoxy-phenyl) propan-2-ylamino]ethyl]phenyl]formamide) at the 1 month checkpoint.

The residual content of each active ingredient, DP3 and the total amount of the formoterol degradation products were measured using validated HPLC/UV-VIS method. A MS detector was used to confirm the molecular weights of the detected degradation products found in each can.

The results, summarized in the following Table 3, confirmed those obtained after 6 months storage at 25° C. and 60% RH.

TABLE 3

Results of the stability test of Example 2 performed on the composition stored for 1 month at 40° C. and 75% relative humidity (RH).

| Can | Valve | Crimping | Residual FF (% w/w) | Residual GLY (% w/w) | Residual BDP (% w/w) | DP3 (% w/w with respect to the theoretical formoterol fumarate content) | Total Amount of Formoterol degradation product (% w/w with respect to the theoretical formoterol fumarate content) |
|---|---|---|---|---|---|---|---|
| FEP coated aluminum | EPDM 1 | Normal | 96.2 | 99.5 | 99.0 | <0.10 | 1.1 |
| FEP coated aluminum | EPDM 1 | Vacuum | 96.2 | 99.2 | 99.7 | <0.10 | 1.3 |
| FEP coated aluminum | EPDM 2 | Normal | 100.0 | 101.0 | 100.0 | <0.10 | 1.5 |
| FEP coated aluminum | EPDM 2 | Vacuum | 100.1 | 101.0 | 99.7 | <0.10 | 1.5 |
| FEP coated aluminum | EPDM 4 | Normal | 98.7 | 99.5 | 100.2 | <0.10 | 1.0 |
| FEP coated aluminum | EPDM 4 | Vacuum | 98.6 | 99.1 | 99.4 | <0.10 | 0.8 |
| FEP coated aluminum | EPDM 5 | Normal | 99.5 | 100.8 | 99.4 | <0.10 | 1.0 |
| FEP coated aluminum | EPDM 5 | Vacuum | 99.2 | 100.0 | 99.6 | <0.10 | 1.0 |
| Anodized aluminum | EPDM 2 | Normal | 90.4 | 97.0 | 98.3 | 0.47 | 3.2 |
| Plasma coated aluminum 3 | EPDM 2 | Normal | 89.8 | 98.3 | 99.0 | 0.81 | 2.9 |
| Plasma coated aluminum 3 | EPDM 3 | Normal | 94.0 | 99.7 | 100.4 | 0.15 | 1.5 |
| Fluorine passivated aluminum surface | EPDM 2 | Normal | 82.7 | 94.5 | 96.3 | 1.7 | 6.2 |
| Fluorine passivated aluminum surface | EPDM 3 | Normal | 88.0 | 97.3 | 99.4 | 0.98 | 4.6 |

% (w/w), unless specifically defined, relates to the content by weight of each substance with respect to its initial content in the formulation.

Different numbers near each valve or can definitions define different kinds of cans or valves from same or different suppliers as below reported: Valves: EPDM 1 to 3 represent respectively Bespak: RB700, BK700, and BK701; EPDM 4 and 5 represent respectively Aptar 808 and 810. Cans: FEP coated from 3M; Anodized aluminum, Plasma coated aluminum 2 and 3 and fluorine passivated aluminum surface cans from Presspart.

Example 3

Stability of a Triple Combination Aerosol Solution Composition Stored for 6 Months at 25° C. and 60% Relative Humidity (RH) at Different HCl Concentrations A further study was performed to investigate the stability of a triple combination of formoterol fumarate (FF), glycopyrronium bromide (GLY), and beclometasone dipropionate (BDP) in an aerosol solution formulations corresponding to that of Example 1 (Table 1) wherein the amount of 1M hydrochloric acid was changed to the range from 0.200 to 0.240 μg/μL and stored for 6 months at 25° C. and 60% relative humidity (RH), in FEP coated aluminum cans according to the invention (as previously defined), crimped with EPDM valves (kind 2, corresponding to Bespak BK 700).

Sample batches were stored in inverted orientation, deemed the worst case condition for the drug product stability, and 3 canisters for each batch were analyzed for residual content of active ingredients and total formoterol degradation products (including DP3: corresponding to N-(3-bromo)-[2-hydroxy-5-[1-hydroxy-2-[1-(4-methoxy-phenyl) propan-2-ylamino]ethyl]phenyl]formamide) at the 6 months checkpoint.

The residual content of each active ingredient, DP3 and the total amount of the formoterol degradation products were measured using validated HPLC/UV-VIS method. A MS detector was used to confirm the molecular weights of the detected degradation products found in each can.

The results, summarized in the following Table 4, confirmed those obtained after 6 months storage at 25° C. and 60% RH for a more detailed range of amounts of 1M HCl present in the formulation stored in FEP coated cans.

TABLE 4

Results of the stability test of Example 3 performed on the solution composition containing BDP (100 μg/dose), FF dihydrate (6 μg/dose), GLY (12.5 μg/dose), anhydrous ethanol (12% w/w; 8856 μg/dose), HFA 134a (up to 100% w/w), 1M HCl (in variable amounts as below specified) stored for 6 months at 25° C. and 60% relative humidity (RH).

| 1M HCl content (μg/μL) | Crimping | Residual FF (% w/w) | Residual GLY (% w/w) | Residual BDP (% w/w) | DP3 (% w/w with respect to the theoretical formoterol fumarate content) | Total Amount of Formoterol degradation product (% w/w with respect to the theoretical formoterol fumarate content) |
|---|---|---|---|---|---|---|
| 0.200 | Normal | 92.1 | 95.6 | 96.9 | <0.10 | 2.58 |
| 0.213 | Normal | 95.3 | 97.0 | 96.9 | <0.10 | 1.68 |
| 0.222 | Normal | 96.8 | 101.0 | 102.3 | <0.10 | 0.70 |
| 0.227 | Normal | 97.3 | 101.7 | 103.0 | <0.10 | 0.60 |
| 0.231 | Normal | 96.5 | 101.2 | 102.1 | <0.10 | 0.97 |
| 0.236 | Normal | 94.8 | 101.2 | 102.3 | <0.10 | 1.67 |
| 0.240 | Normal | 92.1 | 102.3 | 101.5 | <0.10 | 2.80 |

Example 4

Stability of a Further Triple Combination Aerosol Solution Composition Stored for 6 Months at 25° C. and 60% Relative Humidity (RH)

A study was performed to investigate the stability of a triple combination of formoterol fumarate (FF), glycopyrronium bromide (GLY), and budesonide in an aerosol solution formulation whose composition is shown in Table 5 and which was stored for 6 months at 25° C. and 60% relative humidity (RH), in different kinds of can, crimped with different kinds of valve.

TABLE 5

Composition of the aerosol solution composition of the triple combination of formoterol fumarate (FF) dihydrate, glycopyrronium bromide (GLY), and budesonide. Content % w/w means the percent content by weight of each component with respect to the total weight of the composition.

| Component | Mass in μg, per actuation (63 μL) | Mass in μg/μL | Content % (w/w) |
|---|---|---|---|
| Budesonide | 100 | 1.59 | 0.135 |
| FF dihydrate | 6 | 0.095 | 0.0081 |
| GLY | 12.5 | 0.20 | 0.0169 |
| Ethanol (anhydrous) | 8856 | 140.57 | 12.000 |
| 1M HCl | 14 | 0.22 | 0.0019 |
| HFA 134a | 64811.5 | 1028.75 | 87.820 |

Sample batches were stored in inverted orientation, deemed the worst case condition for the drug product stability, and 3 canisters for each batch were analyzed for residual content of active ingredients and total formoterol degradation products (including DP3: corresponding to N-(3-bromo)-[2-hydroxy-5-[1-hydroxy-2-[1-(4-methoxyphenyl)propan-2-ylamino]ethyl]phenyl]formamide) at the 6 months checkpoint.

The residual content of each active ingredient, DP3 and the total amount of formoterol degradation products were measured using a validated HPLC/UV-VIS method. A mass spectra detector was used to confirm the molecular weights of the detected degradation products found in each can.

The results, summarized in the following Table 6 confirmed that, after 6 months at 25° C./60% relative humidity (RH), the configurations performing the best results in terms of higher active ingredient content (in particular of glycopyrronium bromide and formoterol), the lowest levels of total formoterol degradation products (with respect to the theoretical formoterol fumarate content of 6 μg/actuation) and mainly in degradation product DP3 lower than the limit of quantification of 0.10% w/w (with respect to theoretical formoterol fumarate content of 6 μg/actuation), were those wherein the composition was stored in aluminum cans internally coated with a resin comprising a fluorinated ethylene propylene (FEP) polymer.

The composition of the present invention packaged in cans internally coated with a resin comprising a fluorinated ethylene propylene (FEP) polymer, even in presence of a different inhalation corticosteroid (budesonide in place of BDP) showed degradation product DP3 level lower than the limit of quantification of 0.10% w/w (with respect to the theoretical formoterol fumarate content of 6 μg/actuation), total formoterol degradation product levels lower than 2% w/w (with respect to the theoretical formoterol fumarate content of 6 μg/actuation) and the maintenance of formoterol fumarate, the most instable component of the composition, residual level higher than 95% w/w after storage in the present conditions.

TABLE 6

Results of the stability test of Example 4 performed on the composition stored for 6 months at 25° C. and 60% relative humidity (RH).

| Can | Valve | Crimping | Residual FF (% w/w) | Residual GLY (% w/w) | Residual Budesonide (% w/w) | DP3 (% w/w with respect to the theoretical formoterol fumarate content) | Total Amount of Formoterol degradation product (% w/w with respect to the theoretical formoterol fumarate content) |
|---|---|---|---|---|---|---|---|
| FEP coated aluminum | EPDM 2 | Normal | 97.1 | 99.0 | 100.6 | <0.10 | 0.82 |
| Fluorine passivated aluminum surface | EPDM 2 | Normal | 91.3 | 97.3 | 99.2 | 1.92 | 3.86 |
| Plasma coated aluminum 3 | EPDM 2 | Normal | 94.2 | 96.7 | 98.6 | 0.20 | 0.85 |

Different numbers near each valve or can definitions define different kinds of cans or valves from same or different suppliers as below reported: Valves: EPDM 2 represent Bespak BK700; cans: FEP coated from 3M; Plasma coated aluminum 3 and fluorine passivated aluminum surface cans from Presspart.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A pharmaceutical aerosol solution composition, for use in a pressurized metered dose inhaler, comprising:
   (a) glycopyrronium bromide at a dosage in the range of from 5 to 26 µg per actuation;
   (b) formoterol, or a salt thereof or a solvate of said salt, at a dosage in the range of from 1 to 25 µg per actuation;
   (c) a HFA propellant;
   (d) a co-solvent;
   (e) a stabilizing amount of a mineral acid;
   wherein said composition is contained in an aerosol can internally coated by a resin comprising a fluorinated ethylene propylene (FEP) polymer; and wherein the amount of the degradation product N-(3-bromo)-[2-hydroxy-5-[1-hydroxy-2-[1-(4-methoxyphenyl)propan-2-ylamino]ethyl] phenyl]formamide (DP3)formed, when said composition is stored in accelerated conditions at 25° C. and 60% relative humidity (RH) for at least 6 months, is lower than 0.10% w/w, with respect to the theoretical formoterol fumarate content of 6 µg/actuation.

2. A pharmaceutical aerosol solution composition according to claim 1, wherein said mineral acid is present in an amount of acid equivalent to 0.15 to 0.28 µg/µl of 1M hydrochloric acid.

3. A pharmaceutical aerosol solution composition according to claim 2, wherein said mineral acid is present in an amount of acid equivalent to 0.200 to 0.240 µg/µl of 1M hydrochloric acid.

4. A pharmaceutical aerosol solution composition according to claim 3, wherein said mineral acid is present in an amount of acid equivalent to 0.200 to 0.227 µg/µl of 1M hydrochloric acid in the range from.

5. A pharmaceutical aerosol solution composition according to claim 1, wherein said co-solvent is ethanol.

6. A pharmaceutical aerosol solution composition according to claim 1, wherein said formoterol salt is formoterol fumarate.

7. A pharmaceutical aerosol solution composition according to claim 1, wherein said solvate form of the formoterol salt is formoterol fumarate dihydrate.

8. A pharmaceutical aerosol solution composition according to claim 1, further comprising one or more pharmaceutically active ingredients selected from the group consisting of a beta-2 agonist, an inhalation corticosteroid, an antimuscarinic agent, and a phosphodiesterase-4 inhibitor.

9. A pharmaceutical aerosol solution composition according to claim 8, wherein said inhalation corticosteroid is beclometasone dipropionate, budesonide or its 22R-epimer, ciclesonide, flunisolide, fluticasone propionate, fluticasone furoate, mometasone furoate, butixocort, triamcinolone acetonide, triamcinolone, methylprednisolone, prednisone, loteprednol, or rofleponide.

10. A pharmaceutical aerosol solution composition according to claim 9, wherein said inhalation corticosteroid is beclometasone dipropionate which is present in an amount of 50 to 250 µg per actuation.

11. A pharmaceutical aerosol solution composition according to claim 9, wherein said inhalation corticosteroid is budesonide which is present in an amount of 50 to 250 µg per actuation.

12. A pharmaceutical aerosol solution composition according to claim 1, wherein the level of formoterol degradation products formed, when said composition is stored in accelerated conditions at 25° C. and 60% relative humidity for at least 6 months, is lower than 10% w/w with respect to the theoretical formoterol fumarate content of 6 µg/actuation, and wherein the residual level of formoterol fumarate, when said composition is stored in accelerated conditions at 25° C. and 60% relative humidity for at least 6 months, is higher than 90% w/w with respect to its initial content.

13. A pharmaceutical aerosol solution composition according to claim 12, wherein the overall level formoterol degradation products formed, when said composition is stored in accelerated conditions at 25° C. and 60% relative humidity for at least 6 months, is lower than 2% w/w with respect to the theoretical formoterol fumarate content of 6 µg/actuation, and wherein the residual level of the formoterol fumarate, when said composition is stored in accelerated conditions at 25° C. and 60% relative humidity for at least 6 months, is higher than 95% w/w with respect to its initial content.

14. An aerosol can internally coated by a resin comprising a fluorinated ethylene propylene (FEP) polymer and containing a pharmaceutical aerosol solution composition comprising:
  (a) glycopyrronium bromide at a dosage in the range of from 5 to 26 μg per actuation;
  (b) formoterol, or a salt thereof or a solvate of said salt, at a dosage in the range of from 1 to 25 μg per actuation;
  (c) a HFA propellant;
  (d) a co-solvent;
  (e) a stabilizing amount of a mineral acid; and,
  (f) optionally, an inhalation corticosteroid; and wherein the amount of the degradation product N-(3-bromo)-[2-hydroxy-5-[1-hydroxy-2-[1-(4-methoxyphenyl)propan-2-ylamino]ethyl] phenyl]formamide (DP3) formed, when said composition is stored in accelerated conditions at 25° C. and 60% relative humidity (RH) for at least 6 months, is lower than 0.10% w/w, with respect to the theoretical formoterol fumarate content of 6 μg/actuation.

15. A method for the treatment of an obstructive respiratory disorder selected from the group consisting of asthma and COPD, comprising administering an effective amount of a pharmaceutical aerosol solution composition according to claim 1 to a subject in need thereof.

16. The aerosol can according to claim 14, wherein the can is internally coated by a resin comprising a mixture of fluorinated ethylene propylene (FEP) and polyether sulfone (PES).

* * * * *